(12) United States Patent
Hallier et al.

(10) Patent No.: US 7,953,483 B2
(45) Date of Patent: May 31, 2011

(54) DETECTION OF VENTRICULAR TACHYCARDIA IN AN ACTIVE IMPLANTABLE MEDICAL DEVICE HAVING AN AAI OPERATING MODE

(75) Inventors: Benoit Hallier, Sulsse (BE); Amel Amblard, Chatenay-Malabry (FR)

(73) Assignee: ELA Medical S.A.S., Montrouge (FR)

( * ) Notice: Subject to any disclaimer, the term of this patent is extended or adjusted under 35 U.S.C. 154(b) by 660 days.

(21) Appl. No.: 11/423,110

(22) Filed: Jun. 8, 2006

(65) Prior Publication Data

US 2007/0135849 A1 Jun. 14, 2007

(30) Foreign Application Priority Data

Jun. 9, 2005 (FR) .................................... 05 05851

(51) Int. Cl.
*A61N 1/365* (2006.01)
(52) U.S. Cl. ...................... 607/17; 607/4; 607/9; 607/25
(58) Field of Classification Search .................. 607/4, 9, 607/17, 25
See application file for complete search history.

(56) References Cited

U.S. PATENT DOCUMENTS

| 5,205,283 | A | * | 4/1993 | Olson | 607/4 |
| 5,228,438 | A | * | 7/1993 | Buchanan | 607/18 |
| 5,814,083 | A | | 9/1998 | Hess et al. | |
| 6,324,422 | B1 | * | 11/2001 | Williams et al. | 600/510 |
| 6,871,097 | B1 | | 3/2005 | Strandberg | |
| 2003/0088288 | A1 | | 5/2003 | Armstrong et al. | |
| 2004/0111121 | A1 | | 6/2004 | Brown et al. | |
| 2005/0240235 | A1 | * | 10/2005 | Limousin et al. | 607/9 |

FOREIGN PATENT DOCUMENTS

FR 1 470 836 10/2004

* cited by examiner

*Primary Examiner* — Niketa I Patel
*Assistant Examiner* — Rex Holmes
(74) *Attorney, Agent, or Firm* — Orrick Herrington & Sutcliffe, LLP

(57) ABSTRACT

An active implantable medical device, such as a pacemaker, cardioverter and/ or defibrillator of AAI or AAI/DDD type, with detection of ventricular tachycardiae. This device senses spontaneous ventricular and atrial events; delivers atrial pacing pulses; and is able to apply, after delivery of an atrial pacing pulse, concurrently with sensing ventricular events, a refractory period (PR) and a safety window (FS) of predetermined durations; and determining the beginning of a spontaneous ventricular cycle in response to sensing of a ventricular event out of the safety window (R0, R1, R2, R3). It further includes detecting ventricular tachycardiae in response to sensing of ventricular events occurring both within and out of the safety window, conditioned notably by the detection of a sequence of events including, between two consecutive atrial pacing pulses (A1, A2; A2, A3), one ventricular event occurring within the safety window (r1; r2) and one subsequent ventricular event occurring out of the safety window (R1, R2).

8 Claims, 1 Drawing Sheet

DETECTION OF VENTRICULAR TACHYCARDIA IN AN ACTIVE IMPLANTABLE MEDICAL DEVICE HAVING AN AAI OPERATING MODE

FIELD OF THE INVENTION

The present invention relates to "active implantable medical devices" as such devices are defined by the Jun. 20, 1990 Directive 90/385/CEE of the Counsel of the European Community, and more particularly to single chamber, dual chamber "multisite" (triple or quadruple chamber) pacemakers, defibrillators and/or cardioverter devices that are able to monitor heart activity and to deliver to the heart electrical pulses intended to achieve pacing, resynchronization, cardioversion and/or defibrillation in cases of rhythm disorders they may diagnose.

BACKGROUND OF THE INVENTION

Devices are known that are equipped with pacing and sensing circuits associated with the atrium and the ventricle, that can operate according to two known operating modes, DDD or AAI (the AAI mode being a DDD mode having a lengthened atrio-ventricular delay). These devices may be equipped with a mode called "DDD-AMC" or "AAISafeR" ensuring an automatic mode commutation from DDD to AAI and conversely.

The basic operating mode of a DDD/AAI pacemaker is the AAI mode—or more precisely a "pseudo-AAI" mode—with a single chamber atrial pacing (AAI mode stricto sensu), and a monitoring of ventricular activity. This operating mode is maintained as long as atrio-ventricular conduction is normal, that is, as long as each atrial event (either an atrial detection, corresponding to a spontaneous activity, or an atrial stimulation corresponding to a paced event) is followed by an associated ventricular detection.

In certain circumstances, however, atrio-ventricular blocks ("A-V blocks" or "AVB") may appear, leading to a temporary disorder of depolarization of the ventricle. In this case, as long as several conditions are met, the pacemaker automatically commutes to automatic DDD mode, with parameters that are optimized for this situation of temporary AV block. After disappearance of the AVB, there is a reestablishment of atrio-ventricular conduction, and the pacemaker operation automatically commutes back to AAI mode, as long as several other conditions are met.

As it will be explained, a person of ordinary skill in the art should understand that the invention is not restricted to those devices with automatic mode commutation, but may also apply to devices operating in AAI mode only, insofar as the invention simply proposes to adapt the AAI mode operation without any automatic mode commutation to occur and/or so as to prevent automatic mode commutation towards DDD mode.

Such a pacemaker of AAI or DDD/AAI type is described in EP-A-1 470 836 and its counterpart U.S. Published Pat. Appl. No. 2005/0240235 (commonly assigned herewith to ELA Medical).

The present invention is based upon some observations that have been made while actually following up patients implanted with DDD/AAI pacemakers with automatic mode commutation features. It has been observed that such devices do not react in an optimal manner when certain types of ventricular tachycardiae (VT) appear that have a relatively stable rate that is close to twice the atrial pacing rate. Indeed, as it will be further explained below in the detailed description of FIG. 1, the "safety window" successive to each atrial pacing pulse is hiding one ventricular event out of two. As a result, the device senses a ventricular rate that is half of the actual rate. Therefore, aside from the fact that the ventricular rhythm associated with this tachycardia is not detected, the operation of the device is deceived, which may lead to a false diagnostic leading to an unexpected mode commutation towards DDD mode. Although a DDD mode operation usually has no deleterious effect to the patient, such a commutation is useless and hinders spontaneous atrio-ventricular conduction, which may prevent from diagnosing some other ventricular rhythm disorders for instance, and is in any event undesirable, if not needed.

Clinical observations also show that such a "non-expected" operation due to the hiding of some ventricular events may also occur when in the presence of an AV block, or when the AV cross-talk (hereinafter referred to as "AVCT") condition is happening. This AVCT condition occurs when the device is sensing in the ventricular chamber a signal that is actually coming from a distant electrical stimulus in the atrial chamber. Such a condition needs to be properly detected and characterized so as to be able to diagnose the actual occurrence of an AV block.

OBJECTS AND SUMMARY OF THE INVENTION

It is therefore, an object of the present invention to overcome those problems referred to above, by proposing a device allowing to reveal certain types of VT likely to deceive the device control algorithms, and also to characterize these VT by distinguishing them from AVCT conditions likely to induce similar signals.

The type of device to which the invention applies is a known device of AAI or AAI/DDD type, as disclosed in EP-A-1 470 836 and its counterpart U.S. Published Pat. Appl. 2005/0200235 incorporated by reference herein, comprising: means for sensing spontaneous ventricular and atrial events; means for delivering atrial pacing pulses, means able, following delivery of an atrial pacing pulse, to apply a refractory period and a safety window of predetermined durations, concurrently with means of ventricular sensing; and means for the determination of a beginning of spontaneous ventricular cycle, in response to the detection of a ventricular event out of the safety window.

In one embodiment of the invention, the device also comprises means for the detection of ventricular tachycardiae in response to the detection of ventricular events occurring during the safety window or out of the safety window.

The invention particularly applies to the devices commonly known as having a "DDD with automatic mode commutation" function; that is: devices able to operate in DDD mode and comprising means able to schedule conditional commutation from AAI mode towards DDD mode, and conversely. In this case, the means for detection of ventricular tachycardiae are able to inhibit commutation from AAI mode towards DDD mode in case of detection of a ventricular tachycardia.

More advantageously, the means for detection of ventricular tachycardiae comprise means for preliminary suspicion of a stable ventricular tachycardia, conditioned by: (a) the detection of a series of events including, between two successive atrial pacing pulses, a ventricular event occurring during the safety window, and a subsequent ventricular event occurring out of the safety window.

Following are various advantageous embodiments of the means for detecting a preliminary suspicion:

In the case of a means for measuring coupling intervals between successive ventricular events, the means for detecting a preliminary suspicion of stable ventricular tachycardia are conditioned by: (b) verification of the stability of those measured coupling intervals;

The means for detection of ventricular tachycardiae are able, in case of a confirmed suspicion of a stable ventricular tachycardia, to lengthen the atrial escape interval applied to the means for delivering atrial pacing pulses, and to confirm the occurrence of a ventricular tachycardia in case of an absence of successive ventricular events occurring during the safety window; after confirmation of the presence of a ventricular tachycardia, the atrial escape interval is restored to its previous value;

The means for detecting a preliminary suspicion of stable ventricular tachycardia are conditioned by: (c) the absence of lengthening of the atrial escape interval over a predetermined number of previous cycles, or over a predetermined preceding duration;

In the case of a means for measuring coupling intervals between successive ventricular events and means for analysis of ventricular arrhythmiae in which the measured coupling intervals are compared to a threshold for detection of ventricular tachycardiae, and the means for detecting a preliminary suspicion of stable ventricular tachycardia are conditioned by: (d) the verification that the measured coupling intervals have a duration less than said threshold for detection of ventricular tachycardiae.

BRIEF DESCRIPTION OF THE DRAWINGS

Further, features, characteristics and benefits of the present invention will become apparent to a person of ordinary skill in the art from the following detailed description of a preferred embodiment of the invention, made with reference to the attached figures, in which.

DETAILED DESCRIPTION OF THE INVENTION

The invention can be preferably implemented through an appropriate programming of the internal software of a known device, such as the Symphony and Rhapsody brand implantable devices already marketed by ELA Medical, Montrouge, France. These devices are equipped with a programmable microprocessor, and are comprising circuits intended to acquire, format and process electrical signals collected by implanted electrodes, and deliver pacing pulses to these electrodes. It is also possible to upload towards these devices, by telemetry, pieces of software that will be stored in internal memory and run so as to implement the features of the invention, described in more detail below. Implementing the features of the invention into these devices is easily feasible by the person of ordinary skill in the art, and will therefore not be described in detail.

Figure 1:
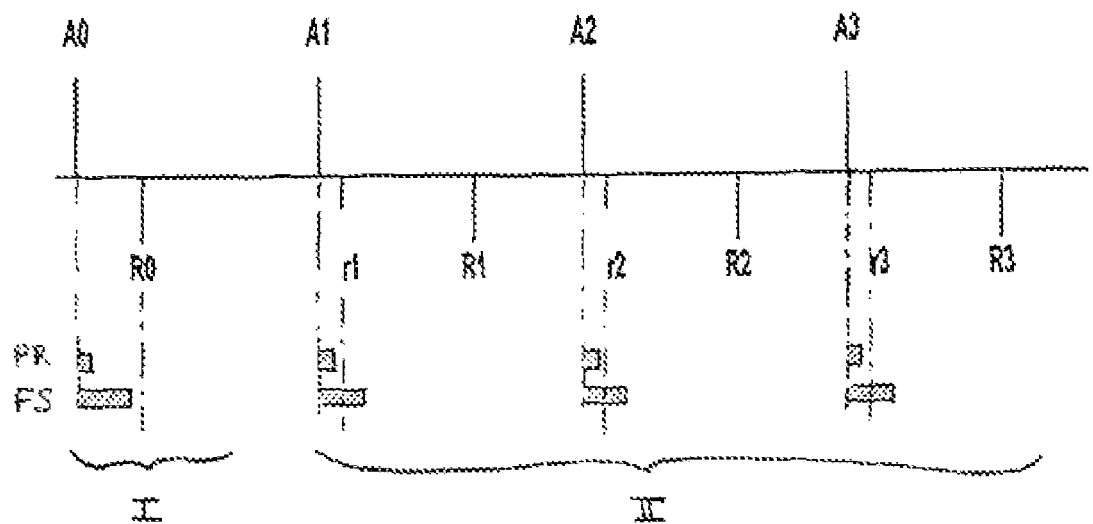
FIG. 1 is a time diagram showing the hiding of some ventricular events in case of a stable VT with a rate twice higher than the atrial pacing rate.

On FIG. 1, the markers A0, A1, A2, A3 show the time position of successive atrial pacing pulses, characteristic of an AAI operating mode. In case of normal atrio-ventricular conduction: that is, in the absence of AV block, the device detects a consecutive ventricular depolarization R0 (region I).

More specifically, after delivery of a pacing pulse, the device concurrently applies to the ventricular sensing circuits:

A refractory period PR during which a "blanking" is applied (or disconnection of sensing circuits so as to mask any disturbance of the amplifiers right after the pacing pulse, this disturbance being caused by the varying impedance loads at the electrode and myocardium interface); and A period FS, referred to as "safety window", typically with a duration of 94 ms, starting from the atrial pacing pulse.

The refractory period PR may advantageously comprise an absolute refractory period of 16 ms, followed by a noise searching period of 16 ms that is retrigerable by steps of 2 ms, up to 32 ms—i.e. this refractory period can last 32 to 48 ms after the atrial pacing pulse. For more details on the way this refractory period is managed, see EP-A-0 962 235 and its counterpart U.S. Pat. No. 6,337,996 (commonly assigned herewith to ELA Medical) and incorporated herein by reference.

Right after the end of refractory period PR, the ventricular sensing circuits are functional, meaning that the device is able to sense the ventricular depolarizations that are occurring during this period of time. However, if a depolarization is sensed before the end of the safety window FS, it will be ignored by the device, because, given the very short delay since the previous atrial pacing pulse, it will be reasonably considered as an artifact or an isolated ventricular extrasystole ("ESV"), which, if taken into account, could interfere with the normal operation of the rhythm analysis algorithm.

For that particular reason, in state-of-the-art devices, such a depolarization is systematically ignored and is not considered as the end (or beginning) of a ventricular cycle, notably for these purposes:

The management of escape intervals and atrio-ventricular delay;

Detection of ventricular arrhythmia features when the device is equipped therewith, notably discrimination between tachycardia and ventricular fibrillation; and The management of potential commutation from AAI mode towards DDD mode.

The present invention is aimed at the particular situation when the device's operation may be misguided when the spontaneous ventricular rate is accelerated until it characterizes a VT, hereinafter referred to as "2:1 stable VT", presenting some specific parameters; more precisely, a VT:

With a stable rate: by "stable rate" or "stable interval", one will understand a rate or a duration, with successive values that are remaining within a range defined as x %, or x ms, or x bpm around a given nominal value; this stability analysis can notably be performed by the ventricular rhythm analysis algorithm described in EP-A-0 838 235 and its counterpart U.S. Pat. No. 5,868,793 (commonly assigned herewith to ELA Medical) which is incorporated herein by reference;

With a rate that is approximately twice as high as the atrial pacing pulse rate; and With one depolarization out of two that occurs within a delay comprised between the end of the refractory period PR and the end of the safety window FS, which may notably happen when the VT has started on a ventricular extrasystole leading to a long coupling interval.

This situation is illustrated by region II on FIG. 1, where the successive ventricular events appear as r1, R1, r2, R2, r3, R3 .... The events R1, R2, R3 ... are sensed by the device and recognized as such. The events r1, r2, r3 ... are hidden by the safety window FS, i.e. they are properly sensed by the device (as they fall after the end of refractory period PR), but are not recognized as such because they fall within the safety window FS. In other words, the safety window of atrial pacing pulses A1, A2, A3 . . . is hiding one ventricular event out of two.

This situation has three disadvantages:
- First, the tachycardia is not sensed as such, for the device is measuring the ventricular rate based upon the unhidden events, and therefore is evaluating a ventricular rate that is half of the actual rate.
- The AV delay determined by the device, i.e. time interval [A1 R1], [A2 R2], [A3 R3] . . . appears too long (compared to the actual delay [A1 r1], [A2 r2], [A3 r3] . . . ), which may deceive the device by letting it confuse with a conduction disorder corresponding to an AV block of type 1, such disorder being characterized by an atrioventricular conduction delay higher than a given threshold value. In such case, a device with automatic mode commutation rapidly triggers commutation towards DDD mode, for example, after 6 cycles showing that same condition.
- When the device comprises a feature of detection of ventricular arrhythmiae (as described in EP-A-1 400 260 and its counterpart U.S. Published Pat. Appl. 2004/0093037 referred to below), the fact the VT is not recognized leads to a dysfunction, as the device mistakenly "sees" a slow, physiological rhythm. That situation is likely to lead to a sensing delay or undersensing of arrythmiae, subsequently with delay or non-delivery of an appropriate therapy (high frequency antitachycardia pacing "ATP", defibrillation or cardioversion shock).

The phenomenum described above may also occur when in the presence of an AV block, an atrio-ventricular cross-talk (AVCT) is happening, the device "seeing" ventricular depolarizations when in fact it is sensing in the ventricle signals coming from atrial pacing pulses.

The invention proposes to overcome these disadvantages, by analyzing the sequence of sensed ventricular events so as to detect a potential 2:1 stable VT, in order to ensure rapid sensing and processing of the VT and prevent a useless commutation towards DDD mode.

The first step is a suspicion of 2:1 stable VT in AAI mode. That suspicion corresponds to the following four conditions:
- a) Detection of a characteristic pattern of the type A1-r1-R1-A2-r2-R2, i.e. in which, during a single atrial cycle, an atrial pacing pulse (A1; A2) is followed by two detections of ventricular events (r1, R1; r2, R2), one within the safety window (r1; r2), and the other out of the safety window (R1; R2);
- b) Optionally, when the device is comprising features of detection of ventricular arrythmiae, it checks that the duration of the ventricular coupling intervals (intervals [R1 r2], [r2 R2] . . . ) is shorter than the programmed value for detection of VT, i.e. that the VT detection threshold has been overshot, this threshold is known in the prior art, under the name of "TDI threshold" (Tachycardia Detection Interval); for more details on this technique, one may refer to EP-A-1 400 260 referred to above;
- c) Stability of ventricular coupling intervals [R1 r2], [r2 R2] . . . , for instance stability at ±x ms, so as to make sure the characteristic pattern is perpetuated; and
- d) No modulation of AEI (see below) has occurred over the last y cycles, for example over the last 20 cycles; that criterion allows to limit the number of modulations when in the presence of the situation described above: of an AV block with AVCT.

When the conditions for suspicion described above are met, in order to confirm the presence of a 2:1 stable VT, the device is modulating the Atrial Escape Interval (AEI) so as to allow detection of two consecutive ventricular depolarizations out of the safety window, within one single atrial cycle (the atrial escape interval (AEI) is the time interval following a detection or a pacing pulse in the atrium, until a pacing pulse is delivered to this atrium, if no spontaneous event has been detected therein). If so, the presence of a 2:1 stable VT is confirmed by the device.

Figure 2:
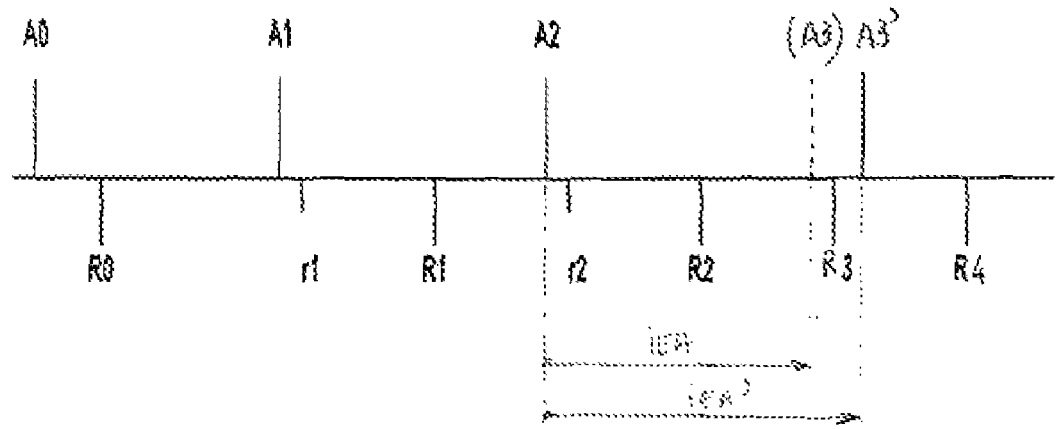
FIG. 2 shows how the modification of the atrial escape interval reveals the depolarizations that would be otherwise hidden, hence confirming the presence of a VT.

This modulation of AEI is illustrated by FIG. 2: for the atrial cycle beginning with A2, with the current AEI, the atrial pacing pulse is delivered at the instant A3, in such a way that the ventricular event r3, post factum to A3, is hidden by the refractory period that is triggered on A3 pacing pulse, as described above in reference to FIG. 1. If the AEI is lengthened up to AEI', then the atrial pacing pulse is delayed towards A3', in such a way that the ventricular event following the event R2 will appear before the end of the AEI, therefore before A3' and out of the safety window of A2, and will therefore be considered as such by the device. In other terms, lengthening of the AEI allows to reveal the ventricular event R3, that used to be hidden in r3 by the safety window.

The lengthening of the AEI has a fixed duration, for example 125 ms. Advantageously, this value is programmable within a range of from 50 to 150 ms. The event R3 that is revealed by lengthening of the AEI being considered as a ventricular extrasystole, the AEI is recycled on that event. Also, as soon as the VT has been unhidden, the AEI is restored to its previous value, so that the device may return to its normal operation.

The device can then take into account the 2:1 stable VT that has been revealed, for example in order to apply an appropriate therapy such as high frequency antitachycardia pacing, in a conventional manner.

Also, in the case of a device with automatic mode commutation, commutation from AAI mode towards DDD mode is inhibited by the detection of VT, the device continuing to analyze the rhythm so as to detect potential actual AV blocks.

One skilled in the art will appreciate that the present invention can be practiced by other than the described embodiments, which are presented for purposes of illustration and not of limitation.

We claim:

1. An active implantable medical device, able to operate in at least one AAI operating mode with ventricular sensing, comprising:
   means for sensing ventricular and atrial spontaneous events;
   means for delivering atrial pacing pulses (A1, A2, A3);
   means able to apply, after delivery of an atrial pacing pulse, concurrently with means for sensing ventricular events, a refractory period (PR) and a safety window (FS) of predetermined durations, the predetermined duration of the safety window being longer than the predetermined duration of the refractory period;
   means for sensing ventricular events occurring out of the safety window (R0, R1, R2, R3) and ventricular events occurring within the safety window after the end of the refractory period (r1, r2, r3) in response to the atrial pacing pulse (A1, A2, A3);
   means for determining the beginning of a spontaneous ventricular cycle in response to sensing of the ventricular events;
   means for measuring ventricular coupling intervals between successive ventricular events of the sensed ventricular events (R1-r2, r2-R2, R2-r3,);
   means for detecting a ventricular tachycardia by analyzing the ventricular coupling intervals; and means for modulating atrial escape interval (AEI) in response to the ventricular coupling intervals to discriminate a stable ventricular tachycardia from an unstable ventricular tachycardia.

2. The device of claim 1, wherein the device also is able to operate in DDD operating mode, and further comprises:
   means for scheduling conditional commutation from AAI mode towards DDD mode and reciprocally, wherein said means for detecting a ventricular tachycardia further comprises means for inhibiting commutation from AAI mode towards DDD mode in response to a detection of a ventricular tachycardia.

3. The device of claim 1, wherein:
   said means for detecting a ventricular tachycardia further comprises means for detecting a preliminary suspicion of a stable ventricular tachycardia, conditioned by the detection of a sequence of events comprising, between two consecutive atrial pacing pulses (A1, A2; A2, A3), one ventricular event occurring during the safety window (rl; r2) and one subsequent ventricular event occurring out of the safety window (R1, R2).

4. The device of claim 3, wherein the means for modulating atrial escape interval (AEI) is able, in response to a suspicion of stable ventricular tachycardia, to:
   lengthen the atrial escape interval (AEI) applied to the means for delivering atrial pacing pulses, and
   confirm the presence of a stable ventricular tachycardia in response to an absence of a consecutive ventricular event occurring during the safety window.

5. The device of claim 4, wherein the means for modulating atrial escape interval (AEI) is able, in response to the stable ventricular tachycardia, to restore the atrial escape interval (AEI) to its previous value.

6. The device of claim 3 further comprising
   means for detecting a preliminary suspicion of a stable ventricular tachycardia conditioned by:
      verification of the stability of said measured ventricular coupling intervals.

7. The device of claim 3, wherein the means for detecting a preliminary suspicion of a stable ventricular tachycardia is conditioned by
   detection of an absence of lengthening of atrial escape interval over a predetermined number of previous cycles or a predetermined previous duration.

8. The device of claim 3, further comprising
   means for analyzing ventricular arrhythmiae, in which the measured ventricular coupling intervals are compared to a threshold of ventricular tachycardiac detection (TDI), wherein said means for detecting a preliminary suspicion of a stable ventricular tachycardiac is conditioned by
   verification that the measured ventricular coupling intervals show a duration that is shorter than said threshold of ventricular tachycardiae detection.

* * * * *